(12) United States Patent
Kubitschke et al.

(10) Patent No.: US 9,580,378 B2
(45) Date of Patent: Feb. 28, 2017

(54) METHOD FOR POST-TREATING POLYOL ESTERS

(71) Applicant: Oxea GmbH, Oberhausen (DE)

(72) Inventors: Jens Kubitschke, Essen (DE);
Thorsten Kreickmann, Essen (DE);
Jörg Arnold, Dinslaken (DE);
Matthias Kramer, Bottrop (DE);
Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 14/915,448

(22) PCT Filed: Aug. 29, 2014

(86) PCT No.: PCT/EP2014/002350
§ 371 (c)(1),
(2) Date: Feb. 29, 2016

(87) PCT Pub. No.: WO2015/036090
PCT Pub. Date: Mar. 19, 2015

(65) Prior Publication Data
US 2016/0207871 A1    Jul. 21, 2016

(30) Foreign Application Priority Data

Sep. 14, 2013   (DE) .................. 10 2013 015 289

(51) Int. Cl.
*C07C 67/60*    (2006.01)
*C07C 67/08*    (2006.01)
*C07C 67/56*    (2006.01)

(52) U.S. Cl.
CPC .............. *C07C 67/60* (2013.01); *C07C 67/08* (2013.01); *C07C 67/56* (2013.01)

(58) Field of Classification Search
CPC .................................................. C07C 69/30
See application file for complete search history.

(56) References Cited

U.S. PATENT DOCUMENTS

| | | | |
|---|---|---|---|
| 2,628,249 A | 2/1953 | Bruno, Jr. | |
| 4,304,925 A | 12/1981 | Watanabe et al. | |
| 5,324,853 A | 6/1994 | Jones et al. | |
| 5,434,294 A | 7/1995 | Pugach et al. | |
| 8,158,816 B2 * | 4/2012 | Frey .................. | C07C 67/08 560/248 |
| 9,006,479 B2 | 4/2015 | Frey et al. | |
| 2012/0190883 A1 * | 7/2012 | Frey .................. | C07C 67/08 560/182 |
| 2013/0035271 A1 | 2/2013 | Daute et al. | |

FOREIGN PATENT DOCUMENTS

| | | |
|---|---|---|
| DE | 1945359 A1 | 3/1971 |
| DE | 3012203 A1 | 10/1980 |
| DE | 4002949 A1 | 8/1991 |
| DE | 102009048775 A1 | 4/2011 |
| DE | 102009060865 A1 | 7/2011 |
| WO | 2007095262 A2 | 8/2007 |

OTHER PUBLICATIONS

International Search Report dated Dec. 15, 2014.
Kirk-Othmer Encyclopedia of Chemical Technology, 3rd edition, 1978, pp. 778-789, vol. 1, John Wiley & Sons.
Kirk-Othmer Encyclopedia of Chemical Technology, 3rd edition, 1981, pp. 496-499, vol. 14, John Wiley & Sons.
Goldsmith, Polyhydric Alcohol Esters of Fatty Acids, Chem. Rev. 1943, 257-349, 33.
International Preliminary Report on Patentability dated Mar. 17, 2016.

* cited by examiner

*Primary Examiner* — Sudhakar Katakam
*Assistant Examiner* — Ana Z Muresan
(74) *Attorney, Agent, or Firm* — Michael W. Ferrell

(57) ABSTRACT

A batchwise process for aftertreatment of polyol esters prepared by reacting polyols of the general formula (II)

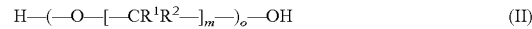

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer from 1 to 10, preferably 1 to 8 and especially 1, 2, 3 or 4, o is an integer from 2 to 15, preferably 2 to 8 and especially 2, 3, 4 or 5, with excess linear or branched aliphatic monocarboxylic acids having 3 to 20 carbon atoms and having a lower boiling point than the polyols used. The process is carried out in the presence of a Lewis acid and in the presence of an adsorbent, while removing the water formed, characterized in that the excess monocarboxylic acid is removed by distillation and water is added to the crude ester obtained at a temperature below the boiling point of water at the particular pressure and the crude ester with added water is aftertreated with avoidance of basic compounds, and the sparingly soluble conversion products and the adsorbent present in the esterification reaction are filtered off.

20 Claims, No Drawings

METHOD FOR POST-TREATING POLYOL ESTERS

CLAIM FOR PRIORITY

This application is a national phase application of PCT/EP2014/002350 FILED Aug. 29, 2014 which was based on application DE 10 2013 015 289.5 FILED Sep. 14, 2013. The priorities of PCT/EP2014/002350 and DE 10 2012 015 289.5 are hereby claimed and their disclosures incorporated herein by reference.

TECHNICAL FIELD

The invention relates to a process for aftertreatment of polyol esters prepared by reaction of linear or branched aliphatic monocarboxylic acids having 3 to 20 carbon atoms with polyols in the presence of a Lewis acid containing at least one element of groups 4 to 14 of the Periodic Table of the Elements as catalyst and in the presence of an adsorbent, by subsequent aftertreatment of the crude ester by addition of water at a temperature below the boiling point of water at the particular pressure.

BACKGROUND

Esters of polyhydric alcohols, also called polyol esters, find a wide range of varying uses in industry, for example as plasticizers or lubricants. The selection of suitable starting materials allows the physical properties, for example boiling point or viscosity, to be controlled, and the chemical properties, such as hydrolysis resistance or stability to oxidative degradation, to be taken into account. Polyol esters can also be tailored to the solution of specific performance problems. Detailed overviews of the use of polyol esters can be found, for example, in Ullmann's Encyclopedia of Industrial Chemistry, 5th edition, 1985, VCH Verlagsgesellschaft, vol. A1, pages 305-319; 1990, vol. A15, pages 438-440, or in Kirk Othmer, Encyclopedia of Chemical Technology, 3rd edition, John Wiley & Sons, 1978, vol. 1, pages 778-787; 1981, vol. 14, pages 496-498.

The use of polyol esters as lubricants is of great industrial significance, and they are used particularly for those fields of use in which mineral oil-based lubricants only incompletely meet the requirements set. Polyol esters are used especially as turbine engine and instrument oils. Polyol esters for lubricant applications are based frequently on 1,3-propanediol, 1,3-butanediol, 1,4-butanediol, 1,2-hexanediol, 1,6-hexanediol, neopentyl glycol, trimethylolpropane, pentaerythritol, 2,2,4-trimethylpentane-1,3-diol, glycerol or 3(4),8(9)-dihydroxymethyltricyclo[5.2.1.0$^{2,6}$]-decane, also known as TCD alcohol DM, as the alcohol component.

Polyol esters are also used to a considerable degree as plasticizers. Plasticizers find a variety of uses in plastics, coating materials, sealing materials and rubber articles. They interact physically with high-polymeric thermoplastic substances, without reacting chemically, preferably by virtue of their dissolution and swelling capacity. This forms a homogeneous system, the thermoplastic range of which is shifted to lower temperatures compared to the original polymers, one result being that the mechanical properties thereof are optimized, for example deformation capacity, elasticity and strength are increased, and hardness is reduced.

A specific class of polyol esters (they are referred to as G esters for short) contains diols or ether diols as the alcohol component, for example ethylene glycol, diethylene glycol, triethylene glycol, tetraethylene glycol, 1,2-propylene glycol or higher propylene glycols. They can be prepared in different ways. In addition to the reaction of alcohol and acid, optionally in the presence of acidic catalysts, further processes are employed in practice to obtain G esters, including the reaction of diol with acid halide, the transesterification of a carboxylic ester with a diol, and the addition of ethylene oxide onto carboxylic acids (ethoxylation). In industrial manufacture, only the direct reaction of diol and carboxylic acid and the ethoxylation of carboxylic acids have become established as production processes, preference usually being given to the esterification of diol and acid. This is because this process can be performed with no particular complexity in conventional chemical apparatus, and it affords chemically homogeneous products. Compared to this, ethoxylation requires extensive and costly technical equipment.

The direct esterification of alcohols with carboxylic acids is one of the basic operations in organic chemistry. In order to increase the reaction rate, the conversion is typically performed in the presence of catalysts. The use of one of the reactants in excess and/or the removal of the water formed in the course of the reaction ensures that the equilibrium is shifted in accordance with the law of mass action to the side of the reaction product, i.e. of the ester, which means that high yields are achieved.

Comprehensive information regarding the preparation of esters of polyhydric alcohols, also including esters of ethylene glycols and fatty acids, and regarding the properties of selected representatives of these compound classes can be found in Goldsmith, Polyhydric Alcohol Esters of Fatty Acids, Chem. Rev. 33, 257 ff. (1943). For example, esters of diethylene glycol, of triethylene glycol and of polyethylene glycols are prepared at temperatures of 130 to 230° C. over reaction times of 2.5 to 8 hours. Suitable catalysts mentioned for the esterification of polyhydric alcohols are inorganic acids, acidic salts, organic sulfonic acids, acetyl chloride, metals or amphoteric metal oxides. The water of reaction is removed with the aid of an entraining agent, for example toluene or xylene, or by introducing inert gases such as carbon dioxide or nitrogen.

The production and the properties of fatty acid esters of the polyethylene glycols are discussed by Johnson (edit.), Fatty Acids in Industry (1989) Chapter 9, Polyoxyethylene Esters of Fatty Acids, and a series of preparative hints are given. Higher diester concentrations are achieved by the increase in the molar ratio of carboxylic acid to glycol. Suitable measures for removing the water of reaction are azeotropic distillation in the presence of a water-immiscible solvent, heating while passing through an inert gas, or performing the reaction under reduced pressure in the presence of a desiccant. When the addition of catalysts is dispensed with, longer reaction times and higher reaction temperatures are required. Both reaction conditions can be made milder by the use of catalysts. In addition to sulfuric acid, organic acids such as p-toluenesulfonic acid and cation exchangers of the polystyrene type are the preferred catalysts. The use of metal powders, such as tin or iron, is also described. According to the teaching from U.S. Pat. No. 2,628,249, color problems in the case of catalysis with sulfuric acid or sulfonic acid can be alleviated when working in the presence of activated carbon.

Further metallic catalysts used to prepare polyol esters are also alkoxides, carboxylates or chelates of titanium, zirconium or tin, for example according to U.S. Pat. No. 5,324,853 A1. Such metal catalysts can be considered as high-temperature catalysts, since they achieve their full activity only at high esterification temperatures, generally above 180° C. They are frequently added not at the start of the esterification reaction, but after the reaction mixture has already been heated up and has reacted partly with elimination of water. In spite of the relatively high reaction temperatures and relatively long reaction times required compared to the conventional sulfuric acid catalysis, crude esters with a comparatively low color number are obtained in the case of catalysis with such metal compounds. Common esterification catalysts are, for example, tetraisopropyl orthotitanate, tetrabutyl orthotitanate, tetrabutyl zirconate or tin(II) 2-ethylhexanoate. Metal traces in the purified polyol esters can impair the use thereof as plasticizers or lubricants since, for example, the electrical conductivity or the stability to atmospheric oxygen is affected. The prior art proposes a number of measures for converting the esterification catalyst to efficiently removable conversion products.

According to the mode of operation described in DE 10 2009 048 775 A1, the esterification of polyols with aliphatic monocarboxylic acids is conducted with a Lewis acid catalyst in the presence of an adsorbent. In the course of the workup of the crude ester, steam treatment is effected, in the course of which Lewis acid catalyst still present is destroyed. By filtration together with the adsorbent, it is possible to remove the catalyst conversion products in a simple manner. The steam treatment is conducted at temperatures generally of 100 to 250° C. and over a period of 0.5 to 5 hours. During the heating period until the attainment of the working temperature, it is necessary to proceed very gently in order to avoid excessive thermal stress on the crude ester. Especially in the case of preparation of polyol esters based on ether diols, for example triethylene glycol or tetraethylene glycol, the conditions of the steam treatment should be set in a controlled manner, in order to prevent unwanted degradation of the ether chain to by-products. Furthermore, the steam treatment for destruction of the Lewis acid catalyst is time-consuming and impairs the product output achieved per unit reactor volume and time.

It is likewise known that it is possible by addition of water and subsequent treatment with alkaline reagents to convert the Lewis acid catalyst to conversion products having good removability. According to the mode of operation disclosed in DE 30 12 203, the crude ester is admixed with 5% to 50% by weight of water, based on the amount of crude ester, and then heated. The heat treatment with water forms well-crystallized conversion products of the Lewis acid catalyst. The water treatment is then followed by the treatment with alkali.

WO 2007/095262 A2 concerns the esterification of 1,3-propanediol which is obtained from renewable raw materials with fatty acids containing 8 to 40 carbon atoms in the molecule, in the presence of metallic catalysts. After the reaction has ended, the catalyst can be removed by treatment with water.

DE 10 2009 060 865 A1 discloses a process for preparing polyol esters which is conducted in the presence of tin compounds. The crude ester obtained is aftertreated by addition of water. After the aqueous phase has been removed, the polyol ester is optionally treated with a sorbent.

DE 40 02 949 A1 discloses a process for workup of a crude esterification mixture which is obtained by continuous esterification in the presence of metallic catalysts. After the unconverted alcohol has been distilled off, the mixture is cooled, activated carbon is added and the residual alcohol is stripped off with steam or nitrogen in the presence of the activated carbon.

According to the procedure from U.S. Pat. No. 5,324,853 A1, the crude esterification mixture is admixed with an aqueous sodium carbonate solution and optionally with activated carbon. This procedure hydrolyzes the metal compounds to insoluble solids, which can be filtered off before the further workup of the crude ester compound.

In the case of workup of a crude ester mixture which is obtained by reaction of polybasic carboxylic acids with monoalcohols in the presence of Lewis acid catalysts, for example of titanium- or tin-containing catalysts too, the prior art recommends a water treatment for catalyst removal. According to U.S. Pat. No. 5,434,294, the crude ester is treated with an aqueous alkaline solution at temperatures between 80 and 150° C. and then filtered through an adsorbent. In the workup method described in DE 1 945 359, the crude ester is first treated with alkali and the free alcohol is removed by a steam distillation. Subsequently, the product is cooled down to a temperature below the boiling point of the water and then admixed with at least 0.5% by weight of water, based on the product to be worked up. By means of this water treatment, precipitates of the catalyst conversion products having good filterability are obtained.

In order to ensure sufficient removal of the Lewis acid catalyst in the form of catalyst conversion products after the esterification reaction has ended, the prior art teaches a steam treatment in the presence of an adsorbent or a treatment with water at temperatures below the boiling point of water at the particular pressure in conjunction with a treatment of basic compounds. Since, however, steam treatment is time-consuming and the conditions have to be controlled, and a treatment with bases, for example with sodium hydroxide or sodium carbonate, additionally introduces salts which have to be removed again in the course of the crude ester workup, there is therefore a need for a process for aftertreatment of polyol esters which is less time-consuming but simultaneously provides the desired polyol ester in adequate quality, such that there is reliable compliance with the required specification values such as residual acid number, water content, hydroxyl number and residual metal content and the polyol esters can have maximum versatility of use.

SUMMARY OF INVENTION

The invention therefore consists in a batchwise process for aftertreatment of polyol esters prepared by reacting polyols of the general formula (II)

$$H-(-O-[-CR^1R^2-]_m-)_o-OH \qquad (II)$$

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer from 1 to 10, preferably 1 to 8 and especially 1, 2, 3 or 4, o is an integer from 2 to 15, preferably 2 to 8 and especially 2, 3, 4 or 5, with excess linear or branched aliphatic monocarboxylic acids having 3 to 20 carbon atoms and having a lower boiling point than the polyols used, in the presence of a Lewis acid selected from the group of titanium, zirconium, hafnium, iron, zinc, boron, aluminum and tin as elements or in the form of compounds thereof as catalyst and in the presence of an adsorbent in an amount of 0.1 to 5, preferably 0.5 to 1.5, parts by weight per 100 parts by weight of a reaction mixture, while removing the water formed, characterized in that the excess monocarboxylic acid is removed by distillation and water is added to the crude ester obtained at a temperature below the boiling point of water at the particular pressure and the crude ester with added water is aftertreated with avoidance of basic compounds, and the sparingly soluble conversion products and the adsorbent present in the esterification reaction are filtered off.

DETAILED DESCRIPTION

The reaction between the polyol and aliphatic monocarboxylic acid starting compounds, depending on the starting materials, sets in within the range from about 120 to 180° C., and can subsequently be conducted to completion in different ways.

One configuration of the esterification reaction involves first heating, proceeding from room temperature to a temperature up to a maximum of 280° C., preferably up to 230° C., and, with the temperature kept constant, lowering the pressure stage by stage proceeding from standard pressure, in order to facilitate the removal of the water of reaction. The selection of the pressure stages, whether one, two or more than two stages, and of the pressure to be established at a particular stage, can be varied over a wide range and matched to the particular conditions.

For example, in a first stage, the pressure can be lowered proceeding from standard pressure first down to 600 hPa and then the reaction can be conducted to completion at a pressure of 300 hPa. These pressure figures are guide values which are appropriately complied with.

In addition to the variation of the pressure, it is likewise also possible to alter the temperature in one, two or more than two stages proceeding from room temperature during the esterification reaction, such that the temperature is increased from stage to stage at constant pressure, typically up to a maximum temperature of 280° C. However, it has been found to be appropriate to heat to a maximum of 280° C. with rising temperature from stage to stage, and also to lower the pressure from stage to stage. For example, the esterification reaction can be conducted proceeding from room temperature in a first stage at a temperature up to 190° C. A reduced pressure down to 600 hPa is likewise applied, in order to accelerate the driving-out of the water of reaction. On attainment of the temperature stage of 190° C., the pressure is lowered once again down to 300 hPa, and the esterification reaction is conducted to completion at a temperature up to 230° C. These temperature and pressure figures are guide values which are appropriately complied with. The temperature and pressure conditions to be established at the particular stages, the number of stages and the particular temperature increase or pressure reduction rate per unit time can be varied over a wide range and adjusted according to the physical properties of the starting compounds and of the reaction products, the temperature and pressure conditions of the first stage being established proceeding from standard pressure and room temperature. It has been found to be particularly appropriate to increase the temperature in two stages and to reduce the pressure in two stages.

The lower limit of the pressure to be established depends on the physical properties, such as boiling points and vapor pressures, of the starting compounds and of the reaction products formed, and is also determined by the plant equipment. Proceeding from standard pressure, it is possible to work stage by stage within these limits with pressures decreasing from stage to stage. The upper temperature limit, typically 280° C., should be complied with in order to avoid the formation of decomposition products, some of which have a damaging effect on color. The lower limit of the temperature stages is determined by the reaction rate, which must still be sufficiently high to conclude the esterification reaction within an acceptable time. Within these limits, it is possible to work stage by stage with temperatures rising from stage to stage.

The particular reaction conditions, such as temperature, reaction time, pressure to be applied or catalyst to be used, should be tailored to the particular polyol ester, in order to force the formation of coloring components into the background and as far as possible to avoid degradation reactions of the polyol ester with a sufficient reaction rate. Especially in the case of polyol esters based on ether diols, for example triethylene glycol or tetraethylene glycol, enhanced degradation of the ether skeleton may set in when the reaction conditions, such as temperature, reaction time and type and amount of catalyst, are not adjusted in a controlled manner to the particular polyol ester.

In the esterification, the polyol is allowed to react with excess monocarboxylic acid which has a lower boiling point than the polyol used and which can be removed by distillation in a simple manner in the subsequent workup of the crude ester. The aliphatic monocarboxylic acid is used in a 10 to 50% molar excess, preferably in a 20 to 40% molar excess, per mole of hydroxyl group to be esterified in the polyol.

The water of reaction formed is distilled out of the reaction vessel in the course of the esterification reaction together with the excess monocarboxylic acid and passed into a downstream phase separator in which monocarboxylic acid and water separate according to their solubility properties. Between the reaction vessel and phase separator, it is likewise possible to install a fractionating column having 1 to 25, preferably 2 to 10 and especially 3 to 6 theoretical plates, in which the water-enriched fraction is passed through the top of the column into the phase separator and the monocarboxylic acid-enriched fraction flows back through the column trays into the reaction vessel.

In some cases, the monocarboxylic acid used also forms an azeotrope with water under the reaction conditions and is capable of removing the water of reaction as an entraining agent. The occurrence of water can be used to monitor the progress of the reaction. The water separated out is removed from the process, while the monocarboxylic acid flows out of the phase separator back into the reaction vessel. The addition of a further organic solvent, such as hexane, 1-hexene, cyclohexane, toluene, xylene or xylene isomer mixtures, which assumes the task of the azeotroping agent, is not ruled out, but it is restricted to a few exceptional cases. The azeotroping agent can be added as early as at the start of the esterification reaction or after the attainment of relatively high temperatures. When the theoretically expected amount of water has been obtained or the hydroxyl number, for example determined to DIN 53240, has fallen below a set value, the reaction is ended and the workup of the crude ester is commenced.

Catalysts used for the esterification of the polyol with the monocarboxylic acid are Lewis acids selected from the group of titanium, zirconium, hafnium, iron, zinc, boron, aluminum and tin as elements in finely distributed form or preferably in the form of compounds thereof, which can be used in solid or liquid form. The term "Lewis acid" in the context of the invention is understood to mean the general standard definition for such elements or compounds having an electron pair gap, as described, for example, in Römpp's Chemie-Lexikon, 8th edition, Franck'sche Verlagshandlung 1983, volume 3, H-L. Suitable compounds are, for example, tin(II) oxide, tin(IV) oxide, tin carboxylates such as tin(II)

2-ethylhexanoate, tin(II) oxalate, tin(II) acetate or tin(IV) acetate, tin(IV) alkoxides such as tetra(methyl) stannate, tetra(ethyl) stannate, tetra(propyl) stannate, tetra(isopropyl) stannate or tetra(isobutyl) stannate, or organotin compounds such as butyltin maleate or dibutyltin dilaurate.

The suitable titanium compounds include alkoxides such as tetra(methyl) orthotitanate, tetra(ethyl) orthotitanate, tetra(propyl) orthotitanate, tetra(isopropyl) orthotitanate, tetra(butyl) orthotitanate, tetra(isobutyl) orthotitanate, tetra(pentyl) orthotitanate or tetra(2-ethylhexyl) orthotitanate; acylates such as hydroxytitanium acetate, hydroxytitanium butyrate or hydroxytitanium pentanoate, carboxylates such as titanium(IV) acetate, titanium(IV) propionate, titanium(IV) butyrate, titanium(IV) pentanoate or titanium(IV) 2-ethyl-hexanoate; or chelates such as tetraethylene glycol titanate or tetrapropylene glycol titanate. It is also possible to successfully use the corresponding zirconium or hafnium compounds, such as tetramethyl orthozirconate, tetraethyl orthozirconate, tetrapropyl orthozirconate, tetraisopropyl orthozirconate, tetrabutyl orthozirconate, tetraisobutyl orthozirconate, tetrapentyl orthozirconate or tetra(2-ethylhexyl) orthozirconate.

Likewise suitable are boric acid and boric esters such as trimethyl borate, triethyl borate, tripropyl borate, triisopropyl borate, tributyl borate or triisobutyl borate.

Likewise suitable are aluminum oxide, aluminum hydroxide, aluminum carboxylates such as aluminum acetate or aluminum stearate, or aluminum alkoxides such as aluminum tributoxide, aluminum tri-sec-butoxide, aluminum tri-tert-butoxide or aluminum triisopropoxide.

It is also possible to use zinc oxide, zinc sulfate and zinc carboxylates such as zinc acetate dihydrate or zinc stearate, and iron(II) acetate or iron(III) hydroxide oxide, as catalysts.

The catalyst can be added to the reaction mixture as early as at the start, or only subsequently with observation of safety measures at elevated temperature, when, for example, the removal of the water of reaction has set in. The catalyst can be added in one portion or a number of portions. It is particularly advisable to add another residual amount of catalyst toward the end of the esterification reaction.

The amount of the esterification catalyst added is $1 \times 10^{-5}$ to 20 mol %, preferably 0.01 to 5 mol %, especially 0.01 to 2 mol %, based on the starting compound added in deficiency, appropriately based on the polyol. In the case of higher amounts of catalyst, cleavage reactions of the polyol esters are to be expected.

Particularly in the case of the preparation of polyolesters based on ether diols, for example triethylene glycol or tetraethylene glycol, in the case of use of high catalyst concentrations toward the end of the reaction and in the phase of the conversion of last residues of free hydroxyl groups, there is a risk of enhanced cleavage of the ether chain, such that the reaction temperature or the pressure to be applied should be adjusted in this case. The higher the catalyst concentration selected is, the lower the reaction temperature or the pressure to be applied should generally be selected, and an optimized temperature and pressure profile should be employed. In the case of excessively low catalyst concentrations, the esterification rate becomes so low that an acceptable conversion is not observed within an acceptable reaction time.

The esterification catalyst can be added in liquid or solid form. Solid catalysts, for example tin(II) oxide, zinc oxide or iron(III) hydroxide oxide are removed after the esterification reaction has ended, in the course of the further workup. If the esterification catalysts are added in the form of liquid compounds, for example tetra(isopropyl) orthotitanate or tetra(butyl) orthotitanate, which are still present dissolved in the reaction mixture after the esterification reaction has ended, these compounds are converted by the inventive aftertreatment to sparingly soluble conversion products which can be removed in a simple manner by filtration together with the adsorbent present in the esterification reaction.

The esterification is conducted in the presence of an adsorbent. This involves using porous high-surface area solid materials which are typically used in chemical practice both in the laboratory and in industrial plants. Examples of such materials are high-surface area polysilicic acids such as silica gels (silica xerogels), silica gel, kieselguhr, high-surface area aluminum oxides and aluminum oxide hydrates, mineral materials such as clays, or carbonates or activated carbon. Activated carbon has been found to be particularly useful. In general, the adsorbent is suspended in finely divided form in the reaction solution, which is agitated by intensive stirring or by introducing an inert gas. This achieves intimate contact between the liquid phase and the adsorbent. The amount of the adsorbent can be adjusted substantially freely and hence according to the individual requirements. Based on 100 parts by weight of the liquid reaction mixture, 0.5 to 5 and preferably 0.1 to 1.5 parts by weight of the adsorbent are used.

Owing to the quality criteria described at the outset for polyol esters, the process steps in the esterification stage with removal of the water of reaction and in the workup of the crude ester are very important process features, since the adjustment of these process steps affects the sensory and optical properties of the end products and residual content of catalyst to a significant degree. More particularly, an optimized process regime affords polyol esters based on ether diols, for example triethylene glycol or tetraethylene glycol, with high purity, and also low color number and high color stability. The structure of the starting materials, of the polyhydric alcohols and of the aliphatic monocarboxylic acids is, in contrast, crucial for the mechanical and thermal properties of the polymer materials plasticized with the polyol esters, and influences the hydrolysis and oxidation stability of lubricants.

The reaction mixture obtained after the reaction has ended comprises, as well as the polyol ester as the desired reaction product, unconverted starting materials, more particularly aliphatic monocarboxylic acid still in excess, since a monocarboxylic acid excess is employed in the esterification reaction. Typically, unconverted starting compounds present in excess are first distilled off, appropriately with application of a reduced pressure.

Subsequently, water is added to the crude ester below the boiling point of water at the particular pressure. The amount of water added is comparatively small and is 0.5% to 5% by weight, preferably 1% to 4% by weight, based on the reaction mixture. It is advisable after the removal of the excess starting compound and after distillative removal of the excess monocarboxylic acid to allow the reaction mixture to cool at standard pressure to a temperature in the range from 40 to below 100° C., preferably to 60 to 90° C., and to add water. Since the amount of water added, based on the reaction mixture, is comparatively small, the water added is preheated only in exceptional cases. The subsequent water treatment is effected within the temperature range from 40 to below 100° C., preferably 60 to 90° C., over a period of 10 minutes to 4 hours, preferably 30 minutes to 2 hours, by vigorous stirring, circulation or introduction of an inert gas. In the water treatment, the thermal energy already introduced into the crude ester is utilized, for example the heat energy introduced during the esterification reaction or the heat energy supplied during the distillative removal of the excess starting compound. Occasionally, heat energy is also additionally supplied during the water treatment, in order to maintain the temperature range from 40 to below 100° C., preferably from 60 to 90° C., during the water treatment.

The addition of water can likewise be effected at elevated pressure above standard pressure. The amount of water added and the treatment time correspond to the standard pressure mode of operation. The treatment temperature is at least 100° C. and is determined by the pressure applied. The upper temperature limit can be set up to below the boiling point of water at the pressure applied, preferably from 100 to 150° C.

It has been found that, surprisingly, the aftertreatment with water according to the mode of operation of the invention, at comparatively low temperatures, allows virtually complete conversion of the Lewis acid catalyst after only a comparatively short treatment time of 10 minutes to 4 hours, preferably 30 minutes to 2 hours, to sparingly soluble conversion products which can be removed easily.

Compared to the process known from DE 10 2009 048 775 A1, in which the Lewis acid catalyst is converted to conversion products by means of a steam treatment, it is possible in accordance with the invention, in the batchwise process regime, to distinctly reduce the residence time of the crude ester in the production plant and hence distinctly increase the space-time yield of the desired polyol ester. The steam treatment is also conducted at higher temperatures, preferably at temperatures of 150 to 220° C., and so there can be unwanted degradation reactions and a deterioration in the color number particularly in the case of prolonged treatment times.

Especially in the case of preparation of polyol esters based on ether diols, for example triethylene glycol and tetraethylene glycol, unwanted degradation of the ether chain is to be expected in the event of excessive thermal stress. Furthermore, there can likewise be cleavage of the ester group during the steam treatment with release of acidic compounds, necessitating a subsequent treatment with basic substances for reliable compliance with the specification value for the neutralization number or acid number, for example determined in accordance with DIN EN ISO 3682/ ASTM D 1613. For instance, DE 10 2009 048 775 A1 explicitly refers to proceeding very gently during the heating period until the working temperature is attained, in order to avoid excessive thermal stress on the polyol ester during the steam treatment and hence to suppress degradation reactions and deteriorations in color number.

These disadvantages can be avoided by means of the inventive treatment with water at a temperature below the boiling point of water at the particular pressure. Because of the comparatively short treatment time and the comparatively low treatment temperatures, there is less risk of deterioration in color number and of cleavage of the ester group and the ether group in the case of the esterification of ether diols, and so it is possible to dispense with treatment with basic reagents in the course of the process for further workup of the crude ester. This advantageously avoids the introduction of alkali metal ions, for example of sodium hydroxide, which subsequently have to be removed in the form of salts. Residual contents of alkali metal ions have an adverse effect on the isolation characteristics of the desired polyol esters. In the aftertreatment process of the invention, the use of basic compounds to lower the acid number or neutralization number is thus dispensed with.

In a further configuration of the aftertreatment of the invention, the water which is recovered by condensation of steam used to generate heat or reduced pressure is used. This water which is used and recovered in the operation of the esterification plant is frequently also referred to as condensate. In this process variant, the use of fresh water is avoided, and hence also the occurrence of additional wastewater. The condensate is also obtained at an elevated temperature and can be mixed into the crude ester at the required treatment temperature without prior additional heating.

The aftertreatment with water according to the invention hydrolyzes the Lewis acid catalyst and converts it to insoluble catalyst conversion products. The residual content of extraneous substances dissolved in the crude ester which are introduced by the use of the Lewis acid catalysts, for example the titanium content, is monitored over time by analytical determinations in accordance with ASTM D 5185. As soon as the residual content of these extraneous substances has fallen below a fixed limit, the crude ester is worked up further.

In one process variant, the insoluble catalyst conversion products and the adsorbent are first filtered off from the crude ester which is then dried.

The filtration is effected in conventional filtration apparatus at standard temperature or at temperatures up to 120° C. The filtration can be assisted by standard filtration aids such as cellulose, silica gel, kieselguhr or wood flour. However, the use thereof is restricted to exceptional cases.

This is followed by the drying of the polyol ester, for example by passing an inert gas through the product at elevated temperature. Steam can additionally be introduced in order to assist the drying operation. It is also possible to simultaneously apply a reduced pressure at elevated temperature and, if necessary, to pass an inert gas through the product. Even without the action of an inert gas, it is possible to work only at elevated temperature or only at relatively low pressure. The particular drying conditions, such as temperature, pressure and duration, can be determined by simple preliminary tests. In general, temperatures in the range from 80 to 250° C., preferably 100 to 180° C., and pressures of 0.2 to 500 hPa, preferably 1 to 200 hPa and especially 1 to 20 hPa are employed. The drying, optionally together with the introduction of water vapor, removes residues of starting compounds, for example monocarboxylic acid, and water.

In an alternative process variant, the crude ester in the presence of the insoluble catalyst products and the adsorbent can first be dried and then filtered.

In some cases, it may be found to be advantageous, after the water treatment and preferably after filtration and before the drying, to subject the polyol ester obtained to a treatment with hydrogen peroxide, for example by the process described in DE 10 2010 027 458 A1 with an aqueous hydrogen peroxide solution. In this case, there then follows a steam treatment, optionally with drying and fine filtration. The steam treatment serves to destroy peroxidic compounds and to remove the water introduced and is generally conducted at standard pressure, although the use of a slightly reduced pressure of appropriately down to 400 hPa is not ruled out. The steam treatment is generally effected at temperatures of 100 to 250° C., preferably of 150 to 220° C. and especially of 170 to 200° C. It is typically conducted over a period of 0.5 to 5 hours.

Light-colored polyol esters are obtained, which also satisfy the other specifications, such as water content, residual acid content, residual content of catalyst constituents and residual content of monoester.

The polyhydric alcohols or polyols used as starting materials for the esterification reaction satisfy the general formula (II)

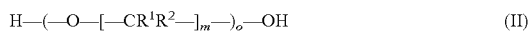

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxy-methyl radical, m is an integer of 1 to 10, preferably 1 to 8 and especially 1, 2, 3 or 4, o is an integer of 2 to 15, preferably 2 to 8 and especially 2, 3, 4 or 5.

Suitable polyols which can be converted to light-colored polyol esters in the esterification reaction are, for example, ditrimethylolpropane or dipentaerythritol.

Useful further polyols include the oligomers of ethylene glycol and 1,2-propylene glycol, especially the ether diols di-, tri- and tetraethylene glycol or dipropylene glycol, tripropylene glycol or tetra-propylene glycol. Ethylene and propylene glycols are industrially produced chemicals. The base substance for preparation thereof is ethylene oxide and propylene oxide, from which 1,2-ethylene glycol and 1,2-propylene glycol are obtained by heating with water under pressure. Diethylene glycol is obtained by ethoxylation from ethylene glycol. Triethylene glycol is obtained, like tetraethylene glycol, as a by-product in the hydrolysis of ethylene oxide to prepare ethylene glycol. Both compounds can also be synthesized by reacting ethylene glycol with ethylene oxide. Dipropylene glycol, tripropylene glycol, tetrapropylene glycol and higher propoxylation products are obtainable from the multiple addition of propylene oxide onto 1,2-propylene glycol.

To obtain light-colored polyol esters in the esterification reaction, linear or branched, aliphatic monocarboxylic acids having 3 to 20 carbon atoms in the molecule are used. Even though preference is given to saturated acids in many cases, depending on the particular field of use of the plasticizers or lubricants, it is also possible to use unsaturated carboxylic acids as a reaction component for ester synthesis. Examples of monocarboxylic acids as components of polyol esters are propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, cyclohexane-carboxylic acid, 2-ethylhexanoic acid, n-nonanoic acid, 2-methyloctanoic acid, isononanoic acid, 3,5,5-trimethylhexanoic acid, 2-propylheptanoic acid, 2-methylundecanoic acid, isoundecanecarboxylic acid, tricyclodecanecarboxylic acid and isotridecane-carboxylic acid. The novel process has been found to be particularly useful for the aftertreatment of polyol esters of the oligomeric ethylene glycols and of the oligomeric propylene glycols with $C_4$- to $C_{13}$- or $C_5$- to $C_{10}$-monocarboxylic acids, and for aftertreatment of polyol esters based on ditrimethylolpropane.

The polyol esters of ethylene glycol and the oligomers thereof are outstandingly suitable as plasticizers for all common high-polymeric thermoplastic substances. They have been found to be particularly useful as an additive to polyvinyl butyral which is used admixed with glycol esters as an intermediate layer for production of multilayer or composite glasses. They can likewise be used as coalescence agents or film-forming assistants in aqueous dispersions of polymers which find various uses as coating materials. By the aftertreatment process of the invention, it is possible in a simple manner to prepare polyol esters having excellent color properties which also satisfy further quality demands, such as low odor, a low acid number and low catalyst impurities. The process of the invention is particularly suitable for aftertreatment of triethylene glycol di-2-ethylhexanoate (3G8 ester), tetraethylene glycol di-n-heptanoate (4G7 ester), triethylene glycol di-2-ethylbutyrate (3G6 ester), triethylene glycol di-n-heptanoate (3G7 ester) or tetraethylene glycol di-2-ethylhexanoate (4G8 ester).

The process of the invention is performed batchwise in the reaction apparatus typical for chemical technology. Useful apparatus has been found to be stirred tanks, including in the form of a stirred tank cascade, or reaction tubes.

The examples which follow illustrate the process of the invention in detail.

WORKING EXAMPLES

Example 1

Preparation of Triethylene Glycol di-2-ethylhexanoate (3G8 Ester) with Subsequent Water Treatment A heatable four-neck flask provided with stirrer, internal thermometer and water separator was initially charged with 1.66 mol of triethylene glycol and 4.33 mol of 2-ethylhexanoic acid. After addition of 0.025% by weight of the titanium catalyst Tyzor® TPT, based on the total mass, and 1% by weight of activated carbon, based on the triethylene glycol input, the reaction mixture was heated to a temperature of 220° C. at 600 hPa, and water of reaction formed was removed. After a reaction time of two hours in this stage, the pressure was lowered to 400 hPa and the temperature was left at 220° C. The course of the reaction was monitored by continuous weighing of the water of reaction discharged by means of the water separator and by sampling and gas chromatography analysis of the samples. The total reaction time was 7 hours. Subsequently, the excess 2-ethylhexanoic acid was removed by distillation at a bottom temperature of 110-210° C. and a pressure of 1 hPa.

After addition of 3% by weight of water, based on the crude ester, the crude product was stirred at 90° C. over the course of 60 minutes and then filtered. Triethylene glycol di-2-ethylhexanoate was obtained with a titanium content below the detection limit of 0.5 ppm (determination of the titanium content in accordance with ASTM D 5185). The results of the gas chromatography analysis (% by weight) and the neutralization number measured (DIN EN ISO 3682/ASTM D 1613) are compiled in table 1 below.

TABLE 1

Aftertreatment of triethylene glycol di-2-ethylhexanoate (3G8 ester) with water

| Property: | Input | Acid removal | [1-A] |
|---|---|---|---|
| Gas chromatography analysis (% by weight) | 3G8 ester after esterification for 7 hours | 3G8 ester after 2-ethylhexanoic acid removal | 3G8 ester after water treatment, 3% by weight of water, 60 minutes, 90° C. |
| First fraction | 0.1 | 0.1 | — |
| 2-Ethylhexanoic acid | 16.7 | 0.1 | 0.1 |
| Triethylene glycol | 0.1 | — | — |
| Triethylene glycol mono-2-ethylhexanoate | 1.5 | 0.9 | 1.0 |
| Diethylene glycol di-2-ethylhexanoate | 0.4 | 0.5 | 0.5 |
| Triethylene glycol di-2-ethylhexanoate | 79.8 | 97.4 | 97.4 |
| Remainder | 1.4 | 1.0 | 1.0 |
| Neutralization number (mg KOH/g, DIN EN ISO 3682/ASTM D 1613) | | 0.1 | 0.1 |
| Titanium content (ppm, ASTM D 5185) | | 20 | <0.5 |

Example 2

Aftertreatment with Water; Comparison of Different Amounts of Water and Treatment Times For the experiments which follow, a triethylene glycol di-2-ethylhexanoate prepared according to example 1 was used, which had a comparatively high titanium content of 80 ppm after removal of the excess 2-ethylhexanoic acid. The amounts of water used for the aftertreatment, based on crude ester, the treatment times employed and the gas chromatography contents determined (% by weight), and also the Hazen color number according to DIN ISO 6271 and titanium content according to ASTM D 5185 are compiled in the table which follows.

TABLE 2

Aftertreatment of triethylene glycol di-2-ethylhexanoate (3G8 ester) with different amounts of water and for various treatment times

| Property: | Input | [2-A] | [2-B] | [2-C] |
|---|---|---|---|---|
| Gas chromatography analysis (% by weight) | 3G8 ester | 3G8 ester 10% by wt. of water 60 minutes 90° C. | 3G8 ester 3% by wt. of water 30 minutes 90° C. | 3G8 ester 3% by wt. of water 60 minutes 90° C. |
| First fraction | 0.1 | — | 0.1 | 0.1 |
| 2-Ethylhexanoic acid | 1.1 | 1.1 | 1.2 | 1.2 |
| Triethylene glycol | — | — | — | — |
| Triethylene glycol mono-2-ethylhexanoate | 0.5 | 0.5 | 0.6 | 0.4 |
| Diethylene glycol di-2-ethylhexanoate | 0.2 | 0.1 | 0.1 | 0.1 |
| Triethylene glycol di-2-ethylhexanoate | 97.2 | 97.3 | 97.1 | 97.3 |
| Remainder | 0.9 | 1.0 | 0.9 | 0.9 |
| Hazen color number (DIN ISO 6271) | 46 | 22 | 29 | 28 |
| Titanium content (ppm, ASTM D5185) | 80 | <0.5 | 1.6 | <0.5 |

It is found that an amount of water of 3% by weight, based on the amount of crude ester, with a treatment time of 1 hour at 90° C., is sufficient to reduce the high Ti content to a value of less than 0.5 ppm (detection limit). The water treatment additionally has an advantageous effect on the Hazen color number, which can be reduced from 46 units in the starting material to 28 units (experiment 2-C).

Rather than fresh water, it is likewise possible to use the water which is recovered by condensation of steam used to generate heat or reduced pressure, frequently referred to as condensate, to deplete the titanium in the crude ester.

Table 3 below shows the conditions for the treatment of the crude ester with condensate and the titanium contents determined in accordance with ASTM D 5185.

TABLE 3

Aftertreatment of triethylene glycol di-2-ethylhexanoate (3G8 ester) with condensate at 75° C.

| Property: | Input | [2-D] | [2-E] |
|---|---|---|---|
| | | 3% by weight of condensate 45 minutes | 3% by weight of condensate 160 minutes |
| Titanium content (ppm, ASTM D 5185) | 9.6 | 0.8 | <0.5 |
| Titanium content (ppm, ASTM D 5185) | 14.0 | 1.8 | <0.5 |

As the results from table 3 show, the residual titanium contents in the treated crude ester can be distinctly reduced even when condensate is used.

Example 3

Additional Aftertreatment With an Aqueous Hydrogen Peroxide Solution and Immediately Subsequent Steam Treatment According to this version of the experiment, triethylene glycol di-2-ethylhexanoate (3G8 ester) which, after water treatment, had a residual titanium content below the detection limit but was unsatisfactory in terms of the Hazen color number was subjected to an aftertreatment with an aqueous 30% hydrogen peroxide solution. The amount of hydrogen peroxide applied was 0.1% by weight absolute, based on the crude ester treated. The hydrogen peroxide treatment was followed immediately thereafter by a steam treatment with subsequent drying. The reaction conditions employed, the composition determined by gas chromatography (% by weight) and the characteristics determined are compiled in table 4 below.

TABLE 4

Aftertreatment of triethylene glycol di-2-ethylhexanoate (3G8 ester) with water and subsequent hydrogen peroxide treatment with immediately subsequent steam treatment and drying

| Property: | Input | [3-A] | [3-B] | [3-C] |
|---|---|---|---|---|
| Gas chromatography analysis (% by weight) | 3G8 ester | 3G8 ester 10% by weight of water 60 minutes 90° C. | 3G8 ester 0.1% absolute H₂O₂ 60 minutes 120° C. | 3G8 ester steam treatment for 60 minutes, 160° C.; drying for 120 minutes, 180° C. |
| First fraction | 0.1 | 0.1 | 0.1 | — |
| 2-Ethylhexanoic acid | 1.0 | 0.6 | 0.6 | — |
| Triethylene glycol | — | — | 0.1 | — |
| Triethylene glycol mono-2-ethylhexanoate | 1.4 | 1.3 | 1.3 | 1.1 |
| Diethylene glycol di-2-ethylhexanoate | 0.2 | 0.2 | 0.2 | 0.2 |
| Triethylene glycol di-2-ethylhexanoate | 96.5 | 96.9 | 96.4 | 97.2 |
| Remainder | 0.8 | 0.9 | 1.3 | 1.5 |
| Hazen color number (DIN ISO 6271) | 86 | 57 | 13 | 17 |
| Neutralization number (mg KOH/g, DIN EN ISO 3682/ASTM D 1613) | 3.1 | 3.1 | 3.2 | 0.1 |
| Hydroxyl number (mg KOH/g, DIN 53240) | 3.7 | 3.2 | 4.7 | 1.9 |
| Titanium content (ppm, ASTM D 5185) | 15 | <0.5 | <0.5 | <0.5 |

The invention claimed is:

1. A batchwise process for aftertreatment of polyol esters prepared by reacting polyols of the general formula (II)

$$H-(-O-[-CR^1R^2-]_m-)_o-OH \quad (II)$$

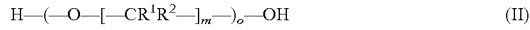

in which $R^1$ and $R^2$ are each independently selected from the group consisting of hydrogen, an alkyl radical having 1 to 5 carbon atoms or a hydroxyalkyl radical having 1 to 5 carbon atoms, m is an integer from 1 to 10, o is an integer from 2 to 15, with excess of linear or branched aliphatic monocarboxylic acids having 3 to 20 carbon atoms and having a lower boiling point than the polyols used, in the presence of a Lewis acid selected from the group consisting of titanium, zirconium, hafnium, iron, zinc, boron, aluminum and tin as elements or in the form of compounds thereof as catalyst and in the presence of an adsorbent in an amount of 0.1 to 5 parts by weight per 100 parts by weight of a reaction mixture, while removing the water formed, characterized in that the excess monocarboxylic acid is removed by distillation and water is added to the crude ester obtained at a temperature below the boiling point of water at the particular pressure and the crude ester with added water is aftertreated with avoidance of basic compounds, and the sparingly soluble conversion products and the adsorbent present in the esterification reaction are filtered off.

2. The process as claimed in claim 1, characterized in that water is added in an amount of 0.5% to 5% by weight, based on the polyol ester to be aftertreated.

3. The process as claimed in claim 1, characterized in that the aftertreatment with water is effected under standard pressure at a temperature of 40 to below 100° C.

4. The process as claimed in claim 1, characterized in that the aftertreatment with water is effected above standard pressure and at a temperature of at least 100° C.

5. The process as claimed in claim 1, characterized in that the aftertreatment with water is conducted over a period of 10 minutes to 4 hours.

6. The process as claimed in claim 1, characterized in that the water which is recovered by condensation of steam used to generate heat or reduced pressure is used for the aftertreatment.

7. The process as claimed in claim 1, characterized in that the aftertreatment with water is followed by a further treatment with hydrogen peroxide, immediately followed by a steam treatment.

8. The process as claimed in claim 1 for aftertreatment of triethylene glycol di-2-ethylhexanoate, tetraethylene glycol di-n-heptanoate, triethylene glycol di-2-ethylbutyrate, triethylene glycol di-n-heptanoate or tetraethylene glycol di-2-ethylhexanoate.

9. The process as claimed in claim 1, in which $R^1$ and $R^2$ are each independently hydrogen, an alkyl radical selected from: methyl, ethyl or propyl; or a hydroxyalkyl radical having 1 to 5 carbon atoms.

10. The process as claimed in claim 1, wherein the hydroxyalkyl radical is hydroxymethyl radical.

11. The process as claimed in claim 1, wherein m is an integer from 1 to 8.

12. The process as claimed in claim 1, wherein m is 1, 2, 3 or 4.

13. The process as claimed in claim 1, wherein o is an integer from 2 to 8.

14. The process as claimed in claim 1, wherein o is 2, 3, 4 or 5.

15. The process as claimed in claim 1, wherein the adsorbent is present in an amount of from 0.5 to 1.5 parts by weight per 100 parts by weight of the reaction mixture.

16. The process as claimed in claim 1, characterized in that water is added in an amount of 1% to 4% by weight, based on the polyol ester to be aftertreated.

17. The process as claimed in claim 1, characterized in that the aftertreatment with water is effected under standard pressure at a temperature of from 60 to 90° C.

18. The process as claimed in claim 1, characterized in that the aftertreatment with water is conducted over a period of 30 minutes to 2 hours.

19. The process as claimed in claim 2, characterized in that the aftertreatment with water is effected under standard pressure at a temperature of 40 to below 100° C.

20. The process as claimed in claim 2, characterized in that the aftertreatment with water is effected above standard pressure and at a temperature of at least 100° C.

* * * * *